United States Patent [19]

Heeres et al.

[11] Patent Number: 4,939,162
[45] Date of Patent: Jul. 3, 1990

[54] 1-(2-ARYL-1,3-DIOXON-2-YLMETHYL)-1H-IMIDAZOLES AND 1H-1,2,4-TRIAZOLES

[75] Inventors: Jan Heeres, Vosselaar; Leo Backx, Arendonk, both of Belgium; Adolf Hubele, Magden, Switzerland

[73] Assignee: Janssen Pharmaceutica N.V., Beerse, Belgium

[21] Appl. No.: 315,197

[22] Filed: Feb. 24, 1989

Related U.S. Application Data

[63] Continuation of Ser. No. 933,289, Nov. 20, 1986, abandoned, which is a continuation of Ser. No. 541,472, Oct. 17, 1983, abandoned, which is a continuation of Ser. No. 202,965, Nov. 3, 1980, abandoned, which is a continuation of Ser. No. 53,500, Jun. 29, 1979, abandoned.

[30] Foreign Application Priority Data

Jul. 25, 1978 [CH] Switzerland .......................... 8005/78
Jul. 25, 1978 [CH] Switzerland .......................... 8041/78

[51] Int. Cl.$^5$ .................. A01N 43/653; C07D 405/06
[52] U.S. Cl. ..................................... 514/383; 514/184; 548/101; 548/268.8
[58] Field of Search ................ 548/101, 262; 514/184, 514/383

[56] References Cited

U.S. PATENT DOCUMENTS 3,575,999  4/1971  Godefroi et al. .................... 548/336
4,079,062  3/1978  Van Reet et al. .................... 548/262

FOREIGN PATENT DOCUMENTS 1533705  11/1978  United Kingdom ................ 548/262

*Primary Examiner*—Glennon H. Hollrah
*Assistant Examiner*—Patricia L. Morris

[57] ABSTRACT

Novel 1-(2-aryl-1,3-dioxan-2-ylmethyl)-1H-imidazoles and 1H-1,2,4-triazoles wherein the 1,3-dioxane ring is optionally substituted with 1 to 3 substituents.

6 Claims, No Drawings

1-(2-ARYL-1,3-DIOXON-2-YLMETHYL)-1H-IMIDAZOLES AND 1H-1,2,4-TRIAZOLES

REFERENCE TO RELATED APPLICATIONS

This is a continuation of application Ser. No. 933,289, filed Nov. 20, 1986, now abandoned, which is a continuation of application Ser. No. 541,472, filed Oct. 17, 1983, now abandoned, which in turn is a continuation of application Ser. No. 202,965, filed Nov. 3, 1980, now abandoned, which in turn is a continuation of application Ser. No. 053,500, filed June 29, 1979, now abandoned.

BACKGROUND OF THE INVENTION

In U.S. Pat. Nos. 3,575,999 and 4,079,062 there are described a number of 1-(2-aryl-1,3-dioxan-2-ylmethyl)-1H-imidazoles and 1H-1,2,4-triazoles wherein the 1,3-dioxane moiety is unsubstituted, said compounds displaying antifungal and antibacterial activities. The compounds of the present invention differ from the foregoing essentially by the presence of 1 to 3 alkyl-substituents on the 1,3-dioxane moiety.

DESCRIPTION OF THE PREFERRED EMBODIMENTS

This invention relates to novel 1-(2-aryl-1,3-dioxan-2-ylmethyl)-1H-imidazole and 1H-1,2,4-triazole derivatives having the formula

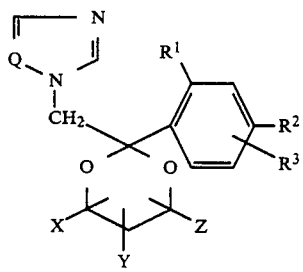

(I)

and the phytopharmaceutically acceptable acid addition salts, metal salt complexes and stereochemically isomeric forms thereof, wherein $R^1$, $R^2$ and $R^3$ are each independently selected from the group consisting of hydrogen and halo, provided that at least one of $R^1$, $R^2$ and $R^3$ is halo;

Q is a member selected from the group consisting of CH and N; and

X, Y and Z are each independently selected from the group consisting of hydrogen and $C_1$–$C_8$-alkyl, provided that at least one of X, Y and Z is other than hydrogen.

Preferred compounds within the scope of the present invention are those wherein X, Y and Z together comprise at most 10 carbon atoms and those wherein $R^1$ and $R^3$ are hydrogen, chloro or bromo and $R^2$ is chloro or bromo.

Particularly preferred compounds within the scope of the present invention are those wherein X, Y and Z together comprise at most 5 carbon atoms, those wherein $R^2$ is chloro and $R^1$ and $R^3$ are hydrogen and those wherein $R^1$ and $R^2$ are both chloro and $R^3$ is hydrogen.

Even more preferred compounds within the scope of the present invention are those wherein none of X, Y and Z has more than 3 carbon atoms.

The most preferred compounds within the scope of the present invention are those wherein $R^1$ and $R^2$ are chloro and $R^3$ is hydrogen, respectively $R^2$ is chloro and $R^1$ and $R^3$ are hydrogen, none of X, Y and Z has more than 3 carbon atoms and two of them being attached to the carbon atom in the 5-position of the 1,3-dioxane nucleus.

As used in the foregoing definitions halo is generic to fluoro, chloro, bromo and iodo; the term "$C_1$–$C_8$ alkyl" is meant to include straight and branched hydrocarbon radicals having from 1 to 8 carbon atoms such as, for example, methyl, propyl, pentyl, 1-methylethyl, 1,1-dimethylethyl, hexyl, heptyl, octyl and the like.

The compounds of formula (I) can generally be prepared by the reaction of an azole of formula (II) wherein Q is as previously described and Me is hydrogen, a tetrasubstituted ammonium ion, e.g., tetra($C_1$–$C_6$-alkyl)ammonium, tri($C_1$–$C_6$-alkyl)ammonium and the like, or, preferably a metal atom, e.g., potassium, sodium and the like, with a halogenide of formula (III) wherein $R^1$, $R^2$, $R^3$, X, Y and Z are as previously described and T is halo, preferably chloro, bromo or iodo.

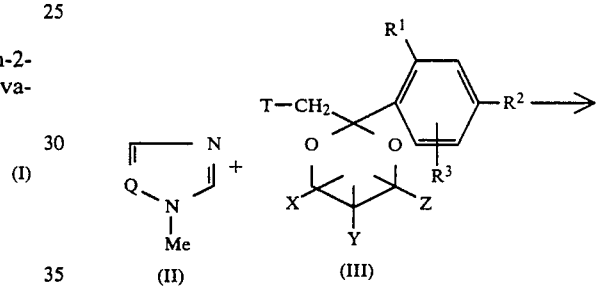

The reaction of (II) with (III) is preferably carried out in a relatively polar, reaction-inert organic solvent, such as, for example, N,N-dimethylformamide, N,N-dimethylacetamide, dimethylsulfoxide, acetonitrile, benzonitrile and the like. Such solvent can be used in combination with other reaction-inert solvents, e.g. aliphatic or aromatic hydrocarbons such as, for example, benzene, methylbenzene, dimethylbenzene, hexane, petroleumether, chlorobenzene, nitrobenzene and the like. When said T represents chloro or bromo it may be advantageous to conduct the reaction in the presence of an alkali metal iodide, such as sodium or potassium iodide, to enhance the reaction rate. Elevated temperatures of from about 30° to about 220° C., preferably from about 80° to about 170° C. are appropriate and conveniently the reaction is carried out under reflux.

When Me represents hydrogen the reaction is carried out in the presence of a base. Suitable bases which may be utilized include alkali metal oxides, hydroxides, carbonates and hydrogen carbonates as well as tertiary amines such as N,N-diethylethanamine, pyridine and the like. In view of its basic properties the azole (II), when added in excess may be used to promote the reaction.

In these and the following preparations the reaction products may be isolated from the medium and, if necessary, further purified according to methodologies generally known in the art, such as, for example, extraction, trituration, crystallization, chromatography and the like.

Suitable salt forming acids are respectively well-tolerated by plants or physiologically acceptable, such as, for example, inorganic acids, e.g., hydrochloric-, hydrobromic-, hydroiodic-, sulfuric-, phosphoric-, phosphonic-, nitric- and the like acids, organic acids, e.g., trifluoroacetic-, trichloroacetic-, benzenesulfonic-, methanesulfonic-, and the like acids.

Metal salt complexes of formula (I) may be obtained by the complexation-reaction of an azole of formula (I) with an organic or inorganic metal salt such as, for example, hydrohalides, nitrates, sulfates, phosphates, 2,3-dihydroxybutanedioates and the like of copper, manganese, zinc, iron and the like transition metals, which may be present in each of their possible valencies.

Stoechiometrically defined metal salt complexes may be prepared by dissolving a compound of formula (I) in a water-miscible solvent (e.g. warm ethanol, methanol, 1,4-dioxane or N,N-dimethylformamide) and adding thereto an aqueous solution of the desired metal salts such as, for example, $CuSO_4.5H_2O$, $Mn(NO_3)_2.4H_2O$, $FeCl_3.6H_2O$ and the like.

The foregoing enumerations are intended to illustrate and not to limit the scope of the present invention.

The intermediates of formula (II), used as starting materials in the foregoing reactions, are generally known in the art.

The intermediates of formula (III) may be prepared according to art-known methodologies of preparing such or similar compounds such as, for example, by acetalizing an appropriate acetophenone derivative of formula (IV) with an appropriate 1,3-diol of formula (V) followng art-known acetalizing procedures.

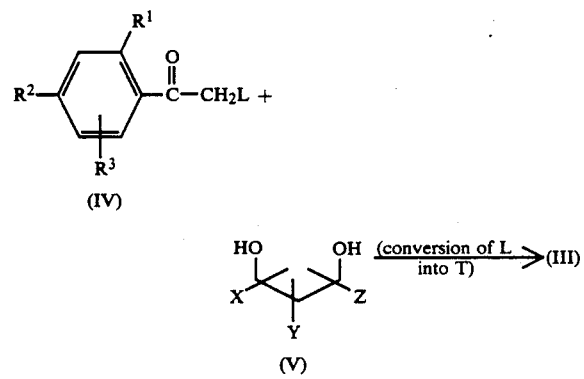

In the foregoing reaction-scheme $R^1$, $R^2$, $R^3$, X, Y and Z are as previously defined and L represents hydrogen or a radical T. When L represents hydrogen, this L-group is converted into a halo group following art-known halogenating procedures, before, during or after the acetalization. The acetalization-reaction is easily carried out by stirring and heating the reactants together in a suitable reaction-inert solvent, e.g., benzene, methylbenzene and the like, preferably in the presence of a catalytic amount of an appropriate acid, e.g., 4-methylbenzenesulfonic acid and the like. Most preferably, the reaction is carried out under azeotropic destillation of the water which is liberated during the course of the reaction. Alternatively the acetals of formula (III) may be derived from other cyclic- or aliphatic acetals by reacting the latter with an excess of the 1,3-diol (V), corresponding to the desired acetal.

From formula (I) it is evident that the compounds of this invention have at least one asymmetric carbon atom and that several compounds have one or more additional asymmetric carbon atoms within the 1,3-dioxane nucleus, due to the presence of X, Y and Z substituents, and consequently they can exist under different stereochemically isomeric forms. The stereochemically isomeric forms of (I) and the phytopharmaceutically acceptable acid addition salts and metal salt complexes thereof are intended to be within the scope of this invention.

The diastereomeric racemates of (I) may be obtained separately by conventional methods. Appropriate methods which may advantageously be employed therefore include, for example, selective crystallization and chromatographic preparation, e.g., column-chromatography.

Since the stereochemical configuration is already fixed in the intermediates (III) it is also possible to separate the diastereomeric racemates at this stage, whereupon the corresponding forms of (I) may be derived therefrom in the previously indicated manner. The separation of the diastereomeric racemates of such intermediates may be performed by conventional methods as described hereabove for the separation of the diastereomeric racemates of the compounds (I).

Particularly, the compounds of formula (I) possess a very advantageous antimicrobial spectrum, rendering them useful for the protection of crops without causing undesired side-reactions.

Examples of crops within the scope of this invention are the followings: cereals, maize, rice vegetables, sugar-beet, soybeans, ground-nuts, fruit-trees, ornamentals, grapevines, hops, cucurbitaceae (gherkins, cucumbers, melons), solanaceae such as potatoes, tobacco and tomatoes, as well as bananas, cocoa and rubber.

The compounds of formula (I) can be used to reduce or destroy fungal growth on plants of thesee or related crops or on parts of such plants (e.g., fruits, blossoms, foliage, stams, tubers, roots), whereby the newly outgrowing parts of such plants are also protected against fungal attack. The compounds of this invention are active against phytophathogenic fungi belonging to the following classes: Ascomycetes (e.g. Erysiphaceae, Fusarium, Venturia, Helminthosporium); Basidiomycetes, such as particularly rust-fungi (e.g. Puccinia); Fungi imperfecti (e.g. Moniliales etc., Cercospora and Botrytis) and Oomycetes belonging to the class of the Phytomycetes such as, for example, Phytophthora and Plasmopara. They can further be used as seed-dressings for the treatment of seed (e.g. fruits, tubers, grains) and cuttings to protect them from fungal infection, and against fungi occuring in the soil.

Botrytis species (*Botrytis cinerea, Botrytis allii*) cause extensive economical damages with greymold to vines, strawberries, apples, bulbs and the like fruit and vegetables.

The compounds of formula (I) can be used alone or in admixture with appropriate carriers and/or additives. Appropriate carriers and additives can be solid or fluid and are generally known in the art of formulating, such as, for example, natural amd regenerated mineral substances, solvents, dispersants, wetting agents, adhesives, thickners, binders or fertilizers.

The concentration of the active ingredient in commercial preparations can vary from about 0.1 to about 90%.

For their application the compounds of forula (I) can be formulated in the following composition-forms (whereby suitable concentrations of the active ingredient are indicated within brackets):

solid compositions: dusts
(up to 10%), granulates, coated granulates, impregnated granulates and homogeneous granulates, pellets (from 1 to 80%);

liquid compositions:
(a) water-dispersible concentrates: wettable powders and pastes (25-90% in commercial form, 0.01-15% in the ready for use solution); emulsion- and solution concentrates (10-50%; 0.01-15% in ready for use solution);
(b) solutions (0.1-20%); aerosols.

If desired, in order to extend their spectrum of activity the compounds of formula (I) may be combined with other appropriate pesticides such as, for example, fungicides, bactericides, insecticides, acaricides, herbicides, plant-growth regulators and the like.

The following examples are intended to illustrate and not to limit the scope of the present invention. All temperatures are give in degrees Celsius.

A.

EXAMPLES OF CHEMICAL PREPARATIONS

EXAMPLE I

To a stirred sodium methoxide solution, prepared starting from 3.7 parts of sodium in 40 parts of methanol, are added 10.8 parts of 1H-imidazole and 270 parts of N,N-dimethylformamide. The methanol is distilled off till internal temperature of 150° C. Then there are added 19 parts of A+B-2-(bromomethyl)-2-(2,4-dichlorophenyl)-5-ethyl-1,3-dioxane and the whole is stirred and refluxed for 5 hours. The reaction mixture is cooled and poured onto water. The product is extracted three times with 1,1'-oxybisethane. The combined extracts are washed with water, dried, filtered and evaporated. The residue is purified by column-chromatography over silica gel: a first fraction is collected by elution with a mixture of trichloromethane and 2% of methanol. The eluent is evaporated and the residue is converted into the nitrate salt in 4-methyl-2-pentanone and 2,2'-oxybispropane. The salt is filtered off and crystallized from a mixture of 4-methyl-2-pentanone and 2,2'-oxybispropane, yielding 5.8 parts (26.5%) of A+B-1-[2-(2,4-dichlorophenyl)-5-ethyl-1,3-dioxan-2-ylmethyl]-1H-imidazole nitrate; mp. 145.1° C.

EXAMPLE II (a) A mixture of 1-(2,4-dichlorophenyl)ethanone, 35 parts of 2-ethyl-1,3-hexanediol, 2 parts of 4-methylbenzenesulfonic acid and 400 parts of methylbenzene is refluxed with a water-separator. After cooling the reaction mixture is washed twice with 200 ml of water, dried on sodium sulfate, filtered and evaporated. To a refluxing solution of the residual oil in methylbenzene is slowly added 33.6 parts of bromine in such a ratio that the reaction mixture decolorizes spontaneously and the mixture is subsequently refluxed during 1 hour. The cooled reaction mixture is washed twice with water, dried, filtered and evaporated. The residual oil, comprising 2-(bromomethyl)-2-(2,4-dichlorophenyl)-5-ethyl-4-propyl-1,3-dioxane, is purified by destillation; bp. 150°-153° C./0.03 Torr.

(b) 23 parts of 2-(bromomethyl)-2-(2,4-dichlorophenyl)-5-ethyl-4-propyl-1,3-dioxane, 5.6 parts of imidazole and 100 parts of dimthylsulfoxide are mixed with 9.3 parts of potassium tert.butoxide and the whole is stirred during 16 hours at 130° C. The cooled mixture is poured onto 500 parts of water and extracted 3 times with 300 parts of 1,1'-oxybisethane. The combined organic layers are washed with 300 parts of water, dried and evaporated. The residual oil is purified by column-chromatography over silica gel using ethyl acetate as eluent. The pure fractions are collected and the eluent is evaporated, yielding a diastereomeric mixture of 1-[2-(2,4-dichlorophenyl)-5-ethyl-4-propyl-1,3-dioxan-2-ylmethyl]-1H-imidazole as a brown oil; $n_D^{23}$: 1.5486.

Following the procedure described hereabove and using equivalent amounts of the appropriate starting materials there are prepared:

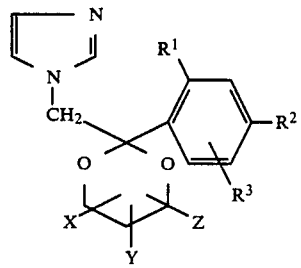

| Compound no. | $R^1$ | $R^2$ | $R^3$ | X,Y,Z | Salt/Base | Melting point in °C. |
| --- | --- | --- | --- | --- | --- | --- |
| 1.1 | Cl | Cl | H | 5-$C_2H_5$,H,H | — | oil |
| 1.2 | Cl | Cl | H | 5-$C_2H_5$,H,H | $HNO_3$ | 145.1 |
| 1.3 | Cl | Cl | H | 5-$C_3H_7$,H,H | — | — |
| 1.4 | Cl | Cl | H | 5-$C_4H_9$,H,H | — | — |
| 1.5 | Cl | Cl | H | 5-$C_6H_{13}$,H,H | — | — |
| 1.6 | H | Cl | H | 5-$C_2H_5$,H,H | — | oil |
| 1.7 | Cl | Cl | 5-Cl | 5-$C_2H_5$,H,H | — | oil |
| 1.8 | Cl | H | 6-Cl | 5-$C_2H_5$,H,H | $HNO_3$ | — |
| 1.9 | Cl | Cl | H | 5-$CH_3$,5-$C_2H_5$,H | — | oil/$n_D^{23}$ = 1.5502 |
| 1.10 | Cl | Cl | H | 5-$C_2H_5$,5-$C_2H_5$,H | — | bp. 180-190/0.04 Torr |
| 1.11 | Cl | Cl | H | 5-$CH_3$,5-$CH_3$,H | — | bp. 165-170/0.04 Torr |
| 1.12 | H | Cl | H | 5-$CH_3$,5-$C_2H_5$,H | — | oil |
| 1.13 | H | Br | H | 5-$CH_3$,5-$C_2H_5$,H | — | oil |
| 1.14 | H | F | H | 5-$CH_3$,5-$C_2H_5$,H | — | oil |
| 1.15 | Cl | H | 6-Cl | 5-$CH_3$,5-$C_2H_5$,H | — | oil |
| 1.16 | Cl | Cl | H | 5-$CH_3$,5-$C_3H_7$,H | — | oil |
| 1.17 | H | Cl | H | 5-$CH_3$,5-$C_3H_7$,H | — | oil |

-continued

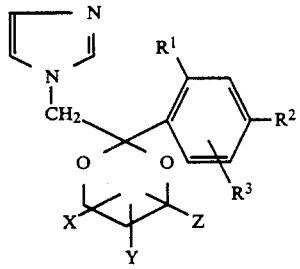

| Compound no. | R¹ | R² | R³ | X,Y,Z | Salt/Base | Melting point in °C. |
|---|---|---|---|---|---|---|
| 1.18 | H | F | H | 5-$CH_3$,5-$C_3H_7$,H | — | 133–137 |
| 1.19 | Cl | Cl | H | 4-$CH_3$,5-$C_2H_5$,H | — | — |
| 1.20 | Cl | Cl | H | 4-$C_2H_5$,5-$C_2H_5$,H | — | — |
| 1.21 | Cl | Cl | H | 4-$C_3H_7$,5-$C_2H_5$,H | — | oil/$n_D^{23}$ = 1.5486 |
| 1.22 | Cl | Cl | H | 5-$CH_3$,5-$CH_3$,H | $CuCl_2$ | — |
| 1.23 | Cl | Cl | H | 5-$CH_3$,5-$CH_3$,H | $ZnCl_2$ | — |
| 1.24 | Cl | Cl | H | 5-$CH_3$,5-$CH_3$,H | $Mn(NO_3)_2$ | — |
| 1.25 | Cl | Cl | H | 5-$C_2H_5$,5-$C_4H_9$,H | — | oil |
| 1.26 | Cl | Cl | H | 5-$C_2H_5$,5-$C_4H_9$,H | $CuCl_2$ | — |
| 1.27 | Cl | Cl | H | 4-$CH_3$,H,H | — | — |
| 1.28 | Cl | Cl | H | 4-$C_2H_5$,H,H | — | — |
| 1.29 | Cl | Cl | H | 4-$C_3H_7$,H,H | — | — |
| 1.30 | Cl | Cl | H | 4-$C_4H_9$,H,H | — | — |
| 1.31 | Cl | Cl | H | 4-$CH_3$,6-$CH_3$,H | — | — |
| 1.32 | Cl | Cl | H | 4-$C_2H_5$,6-$CH_3$,H | — | — |
| 1.33 | Cl | Cl | H | 4-$C_2H_5$,6-$C_2H_5$,H | — | — |
| 1.34 | Cl | Cl | H | 4-$C_3H_7$,6-$C_2H_5$,H | — | — |
| 1.35 | Cl | Cl | H | 4-$CH_3$,6-$CH_3$,H | $HNO_3$ | — |
| 1.36 | Cl | Cl | H | 4-$CH_3$,6-$CH_3$,H | $CuCl_2$ | — |
| 1.37 | Cl | Cl | H | 4-$CH_3$,6-$CH_3$,H | $Mn(NO_3)_2$ | — |
| 1.38 | Cl | Cl | H | 4-$CH_3$,6-$CH_3$,H | $ZnCl_2$ | — |
| 1.39 | Cl | Cl | H | 4-$C_2H_5$,6-$C_2H_5$,H | $HNO_3$ | — |
| 1.40 | Cl | Cl | H | 4-$C_2H_5$,6-$C_2H_5$,H | $CuCl_2$ | — |
| 1.41 | Cl | Cl | H | 4-$C_2H_5$,6-$C_2H_5$,H | $FeCl_3$ | — |
| 1.42 | Cl | Cl | H | 4-$CH_3$,5-$CH_3$,6-$CH_3$ | $HNO_3$ | — |
| 1.43 | H | Cl | H | 4-$CH_3$,5-$CH_3$,6-$CH_3$ | — | — |
| 1.44 | Cl | H | 6-Cl | 4-$CH_3$,5-$CH_3$,6-$CH_3$ | — | — |
| 1.45 | H | F | H | 4-$CH_3$,5-$CH_3$,6-$CH_3$ | — | — |
| 1.46 | Cl | Cl | H | 4-$CH_3$,5-$CH_3$,6-$CH_3$ | $CuCl_2$ | — |
| 1.47 | Cl | Cl | H | 4-$CH_3$,5-$CH_3$,6-$CH_3$ | $Mn(NO_3)_2$ | — |
| 1.48 | H | Cl | H | 4-$CH_3$,4-$CH_3$,6-$CH_3$ | — | — |
| 1.49 | Cl | Cl | H | 4-$CH_3$,4-$CH_3$,6-$CH_3$ | — | — |
| 1.50 | Cl | Cl | H | 4-$CH_3$,4-$CH_3$,6-$CH_3$ | $HNO_3$ | — |
| 1.51 | Cl | Cl | H | 4-$CH_3$,4-$CH_3$,6-$CH_3$ | $CuCl_2$ | — |
| 1.52 | Cl | Cl | H | 4-$CH_3$,4-$CH_3$,6-$CH_3$ | $ZnCl_2$ | — |
| 1.53 | Cl | Cl | H | 4-$CH_3$,4-$CH_3$,6-$CH_3$ | $Mn(NO_3)_2$ | — |
| 1.54 | Cl | H | 6-Cl | 4-$CH_3$,4-$CH_3$,6-$CH_3$ | $HNO_3$ | — |
| 1.55 | Cl | Cl | 5-Cl | 4-$CH_3$,4-$CH_3$,6-$CH_3$ | $HNO_3$ | — |
| 1.56 | H | I | H | 4-$CH_3$,4-$CH_3$,6-$CH_3$ | HCl | — |
| 1.57 | Cl | Br | H | 4-$CH_3$,4-$CH_3$,6-$CH_3$ | $(COOH)_2$ | — |
| 1.58 | Cl | Cl | H | 5-$CH_3$ | — | — |
| 1.59 | Cl | Cl | H | 5-$CH(CH_3)_2$ | — | — |
| 1.60 | Cl | Cl | H | 4-$C_3H_7$,5-$CH_3$,5-$CH_3$ | — | — |

EXAMPLE III

A mixture of 2 parts of 2,2-dimethyl-1,3-propanediol, 1 part of 4-methylbenzenesulfonic acid and 90 parts of methylbenzene is distilled azeotropically to dry for one hour. Then there are added 7.1 parts of 1-[2-(2,4-dichlorophenyl)-2,2-dimethoxyethyl]-1H-1,2,4-triazole 4-methylbenzenesulfonate and stirring at reflux is continued for 6 hours. The reaction mixture is cooled, washed successively with a diluted sodium hydroxide solution and with water, dried, filtered and evaporated. The residue is converted into the nitrate salt in 2,2'-oxybispropane. The salt is filtered off and dried, yielding 4.8 parts (79%) of 1-[2-(2,4-dichlorophenyl)-5,5-dimethyl-1,3-dioxan-2-ylmethyl]-1H-1,2,4-triazole nitrate; mp. 130.6° C.

Following the same procedure and using equivalent amounts of the appropriate starting materials there are also prepared:

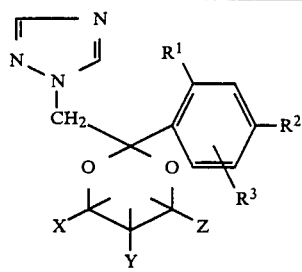

| Compound No. | $R^1$ | $R^2$ | $R^3$ | X,Y,Z | Salt/base | Melting point in °C |
|---|---|---|---|---|---|---|
| 2.1 | Cl | Cl | H | 5-$C_2H_5$,H,H | — | oil |
| 2.2 | Cl | Cl | H | 5-$C_2H_5$,H,H | $HNO_3$ | 160.9 |
| 2.3 | Cl | Cl | H | 5-$C_3H_7$,H,H | — | — |
| 2.4 | Cl | Cl | H | 5-$C_4H_9$,H,H | — | — |
| 2.5 | Cl | Cl | H | 5-$C_6H_{13}$,H,H | — | — |
| 2.6 | H | Cl | H | 5-$C_2H_5$,H,H | — | oil |
| 2.7 | Cl | Cl | 5-Cl | 5-$C_2H_5$,H,H | — | oil |
| 2.8 | Cl | H | 6-Cl | 5-$C_2H_5$,H,H | $HNO_3$ | — |
| 2.9 | Cl | Cl | H | 5-$CH_3$,5-$C_2H_5$,H,H | $HNO_3$ | 134.7 |
| 2.10 | Cl | Cl | H | 5-$C_2H_5$,5-$C_2H_5$,H | $HNO_3$ | 127.2 |
| 2.11 | Cl | Cl | H | 5-$CH_3$,5-$CH_3$ | $HNO_3$ | 130.6 |
| 2.12 | H | Cl | H | 5-$CH_3$,5-$C_2H_5$ | — | oil |
| 2.13 | H | Br | H | 5-$CH_3$,5-$C_2H_5$ | — | oil |
| 2.14 | H | F | H | 5-$CH_3$,5-$C_2H_5$ | — | oil |
| 2.15 | Cl | H | 6-Cl | 5-$CH_3$,5-$C_2H_5$ | — | oil |
| 2.16 | Cl | Cl | H | 5-$CH_3$,5-$C_3H_7$ | $HNO_3$ | 165.4 |
| 2.17 | H | Cl | H | 5-$CH_3$,5-$C_3H_7$ | — | oil |
| 2.18 | H | F | H | 5-$CH_3$,5-$C_3H_7$ | — | oil |
| 2.19 | Cl | Cl | H | 4-$CH_3$,5-$C_2H_5$ | — | oil |
| 2.20 | Cl | Cl | H | 4-$C_2H_5$,5-$C_2H_5$ | — | — |
| 2.21 | Cl | Cl | H | 4-$C_3H_7$,5-$C_2H_5$ | — | oil/$n_D^{23}$ = 1.5412 |
| 2.22 | Cl | Cl | H | 5-$CH_3$,5-$CH_3$ | $CuCl_2$ | — |
| 2.23 | Cl | Cl | H | 5-$CH_3$,5-$CH_3$ | $ZnCl_2$ | — |
| 2.24 | Cl | Cl | H | 5-$CH_3$,5-$CH_3$ | $Mn(NO_3)_2$ | — |
| 2.25 | Cl | Cl | H | 5-$C_2H_5$,5-$C_4H_9$ | — | oil |
| 2.26 | Cl | Cl | H | 5-$C_2H_5$,5-$C_4H_9$ | $CuCl_2$ | — |
| 2.27 | Cl | Cl | H | 4-$CH_3$ | — | — |
| 2.28 | Cl | Cl | H | 4-$C_2H_5$ | — | — |
| 2.29 | Cl | Cl | H | 4-$C_3H_7$ | — | — |
| 2.30 | Cl | Cl | H | 4-$C_4H_9$ | — | — |
| 2.31 | Cl | Cl | H | 4-$CH_3$,6-$CH_3$ | — | oil/$n_D^{23}$ = 1.5505 |
| 2.32 | Cl | Cl | H | 4-$C_2H_5$,6-$CH_3$ | — | — |
| 2.33 | Cl | Cl | H | 4-$C_2H_5$,6-$C_2H_5$ | — | — |
| 2.34 | Cl | Cl | H | 4-$C_3H_7$,6-$C_2H_5$ | — | — |
| 2.35 | Cl | Cl | H | 4-$CH_3$,6-$CH_3$ | $HNO_3$ | — |
| 2.36 | Cl | Cl | H | 4-$CH_3$,6-$CH_3$ | $CuCl_2$ | — |
| 2.37 | Cl | Cl | H | 4-$CH_3$,6-$CH_3$ | $Mn(NO_3)_2$ | — |
| 2.38 | Cl | Cl | H | 4-$CH_3$,6-$CH_3$ | $ZnCl_2$ | — |
| 2.39 | Cl | Cl | H | 4-$C_2H_5$,6-$C_2H_5$ | $HNO_3$ | — |
| 2.40 | Cl | Cl | H | 4-$C_2H_5$,6-$C_2H_5$ | $CuCl_2$ | — |
| 2.41 | Cl | Cl | H | 4-$C_2H_5$,6-$C_2H_5$ | $FeCl_3$ | — |
| 2.42 | Cl | Cl | H | 4-$CH_3$,5-$CH_3$,6-$CH_3$ | $HNO_3$ | — |
| 2.43 | H | Cl | H | 4-$CH_3$,5-$CH_3$,6-$CH_3$ | — | — |
| 2.44 | Cl | H | 6-Cl | 4-$CH_3$,5-$CH_3$,6-$CH_3$ | — | — |
| 2.45 | H | F | H | 4-$CH_3$,5-$CH_3$,6-$CH_3$ | — | — |
| 2.46 | Cl | Cl | H | 4-$CH_3$,5-$CH_3$,6-$CH_3$ | $CuCl_2$ | — |
| 2.47 | Cl | Cl | H | 4-$CH_3$,5-$CH_3$,6-$CH_3$ | $Mn(NO_3)_2$ | — |
| 2.48 | H | Cl | H | 4-$CH_3$,6-$CH_3$,6-$CH_3$ | — | — |
| 2.49 | Cl | Cl | H | 4-$CH_3$,6-$CH_3$,6-$CH_3$ | — | viscous |
| 2.50 | Cl | Cl | H | 4-$CH_3$,6-$CH_3$,6-$CH_3$ | $HNO_3$ | — |
| 2.51 | Cl | Cl | H | 4-$CH_3$,6-$CH_3$,6-$CH_3$ | $CuCl_2$ | — |
| 2.52 | Cl | Cl | H | 4-$CH_3$,6-$CH_3$,6-$CH_3$ | $ZnCl_2$ | — |
| 2.53 | Cl | Cl | H | 4-$CH_3$,6-$CH_3$,6-$CH_3$ | $Mn(NO_3)_2$ | — |
| 2.54 | Cl | H | 6-Cl | 4-$CH_3$,6-$CH_3$,6-$CH_3$ | $HNO_3$ | — |
| 2.55 | Cl | Cl | 5-Cl | 4-$CH_3$,6-$CH_3$,6-$CH_3$ | $HNO_3$ | — |
| 2.56 | H | I | H | 4-$CH_3$,6-$CH_3$,6-$CH_3$ | HCl | — |
| 2.57 | Cl | Br | H | 4-$CH_3$,6-$CH_3$,6-$CH_3$ | $(COOH)_2$ | — |
| 2.58 | Cl | Cl | H | 5-$CH_3$ | — | — |
| 2.59 | Cl | Cl | H | 5-$CH(CH_3)_2$ | — | — |
| 2.60 | Cl | Cl | H | 4-$C_3H_7$,5-$CH_3$,5-$CH_3$ | — | — |

EXAMPLE IV (a) A mixture of 56.7 parts of 1-(2,4-dichlorophenyl)ethanone, 32.4 parts of 1,3-butanediol, 2 parts of 4-methylbenzenesulfonic acid and 400 parts of methylbenzene is stirred and refluxed for 5 hours using a water-separator. After cooling, the reaction mixture is washed with water, dried, filtered and evaporated. To the oily residue, which is taken up in 525 parts of refluxing trichloromethane, are added slowly 49.6 parts of bromine. After completion of the bromine addition the mixture is stirred and refluxed for 1 hour. After cooling, the reaction mixture is washed twice with water, dried, filtered and evaporated. The residual yellow oil is crystallized from 500 parts of cold petroleumether (bp. 40°–60° C.), digerated at low temperature, filtered and washed with cold petroleumether (bp. 40°–60° C.), yielding crystals of 2-(2,4-dichlorophenyl)-2-(bromomethyl)-4-methyl-1,3-dioxane diastereomeric mixture; mp. 69°–70.5° C.

(b) A mixture of 10.8 parts of potassium carbonate, 5.4 parts of 1H-1,2,4-triazole, 20.5 parts of 2-(2,4-dichlorophenyl)-2-(bromomethyl)-4-methyl-1,3-dioxane, 0.2 parts of sodium iodide and 100 parts of dimethylsulfoxide is stirred during 36 hours at 100° C., cooled and poured onto 600 parts of water. The reaction mixture is extracted three times with ethyl acetate and the combined organic layers are washed with 200 parts of water, dried, filtered and evaporated. The residual oil is purified by column-chromatography over silica gel using ethyl acetate as eluent. The pure fractions are collected and the eluent is evaporated, yielding 1-[2-(2,4-dichlorophenyl)-4-methyl-1,3-dioxan-2-ylmethyl]-1H-1,2,4-triazole; $n_D^{22}$: 1.5505.

B.

FORMULATION EXAMPLES

EXAMPLE V

Dusts:

The following substances are used to prepare (a) 5% and (b) a 2% dust:

(a)

5 parts of active substance
95 parts of talc;

(b)

2 parts of active substance
1 part of highly dispersed silicic acid
97 parts of talc.

The active substances are mixed with the carriers and ground and in this form can be processed to dusts for application.

EXAMPLE VI

Granulate:

The following substances are used to prepare a 5% granulate:
5 parts of active substance
0.25 part of epichlorohydrin
0.25 part of cetyl polyglycol ether
3.25 parts of polyethylene glycol
91 parts of kaolin (particle size 0.3–0.8 mm.).

The active substance is mixed with epichlorohydrin and the mixture is dissolved in 6 parts of 2-propanone. Then polyethylene glycol and cetyl polyglycol ether are added. The resultant solution is sprayed on kaolin and the 2-propanone is evaporated in vacuo.

Such a micro-granulate is advantageously used for combating soil fungi.

EXAMPLE VII

Wettable powders:

The following constituents are used to prepare (a) a 70%, (b) a 40%, (c) and (d) a 25% and (e) a 10% wettable powder:

(a)

70 parts of active substance
5 parts of sodium dibutylnaphthylsulfonate
3 parts of naphthalenesulfonic acid/phenolsulfonic acid/formaldehyde condensate (3:2:1).
10 parts of kaolin
12 parts of Champagne chalk.

(b)

40 parts of active substance
5 parts of sodium ligninsulfonate
1 part of sodium dibutylnaphthalenesulfonic acid
54 parts of silicic acid.

(c)

25 parts of active substance
4.5 parts of calcium ligninsulfonate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)

25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)

10 parts of active substance
3 parts of a mixture of the sodium salts of saturated fatty alcohol sulfates
5 parts of naphthalenesulfonic acid/formaldehyde condensate
82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application

EXAMPLE VIII

Emulsifiable concentrates:

The following substances are used to prepare a 25% emulsifiable concentrate:
25 parts of active substance
2.5 parts of epoxidized vegetable oil
10 parts of an alkylarylsulfonate/fatty alcohol polyglycol ether mixture
5 parts of dimethyl formamide
57.5 parts of dimethylbenzene.

By diluting such a concentrate with water it is possible to prepare emulsions of the desired concentration, which are especially suitable for leaf application.

C.
BIOLOGICAL EXAMPLES
EXAMPLE IX

Activity against *Cercospora personata* (=*Cercospora arachidicola*) on ground-nut plants Ground-nut plants, 3 weeks old, are sprayed with a spray broth (containing 0.02% of active substance), prepared from a wettable powder of the active substance. After about 12 hours the treated plants are infected by dusting them with a suspension of conidia of the fungus. The infected plants are then incubated for about 24 hours at 22° C. at a high relative humidity (>90%) and then stood in the glass-house. Fungal infection evaluated 12 days after the day of infection on basis of the number and the extend of the appearing spots. In comparison with untreated plants, those treated with a compound of formula (I), display only limited growth of the fungus or no growth at all.

EXAMPLE X

Activity against *Plasmopara viticola* (Bert. and Curt.)-(Berl. et DeToni) on grapevines Residual-protective action:

3 grapevine seedlings (species "Chasselas"), having 10 leaves, are sprayed with a spray broth (containing 0.06% of active substance) prepared from a wettable powder of the active substance. After drying of the spray, the plants are infected with a suspension of sporangia of the fungus at the under-surface of the leaves and, subsequently, the plants are stood in a wetting room during 8 days. After this period, the untreated plants display invariable fungal growth. The degree of fungal infection is rated on basis of the number and the extend of the appearing spots. The compounds nos. 1.9, 1.16, 1.19, 1.21, 2.9, 2.10, 2.11, 2.16 and similar compounds inhibited completely the growth of the fungus.

EXAMPLE XI

Activity against *Erysiphe graminis* on barley.

(a) Residual-protective action:

Barley plants, about 8 cm in height, are sprayed with a spray broth (containing 0.02% of active substance) prepared from a wettable powder of the active substance. After 3-4 hours the treated plants are dusted with conidia of the fungus. The infected barley plants are then placed in a glass-house at about 22° C. and fungal attack is evaluated 10 days after the day of infection.

(b) Systemic action:

A spray broth (containing 0.006% of the active substance; the amount being proportional with the soil-volume), prepared from a wettable powder of the active substance is administered to barley plants, about 8 cm in height, while care is taken that the external parts of the plants do not enter into contact with the spray. After 48 hours the treated plants are dusted with conidia of the fungus. The infected barley plants are stood in a glass-house at 22° C. and the fungal infection is evaluated after 10 days.

Test (a): The compounds of formula (I) inhibited completely the growth of the fungus. The compounds nos. 1.9, 1.10, 1.11, 1.16, 1.21, 2.9, 2.10, 2.11, 2.16, 2.27, 2.31 and similar compounds display a complete inhibition even at a concentration of 0.0006%.

Test (b): The compounds nos. 1.16, 2.9, 2.11 and similar compounds display complete inhibition of the growth of the fungus.

The compounds of formula (I) and, particularly, the 1H-1,2,4-triazole derivatives are especially active in the protection against mildew (Erysiphe spp.).

EXAMPLE XII

Activity against *Botrytis cinerea* on broad beans

Broad bean plants, about 10 cm in height, are sprayed with a spray broth (containing 0.02% of active substance) prepared from a wettable powder of the active substance. After 48 hours the treated plants are infected with a suspension of conidia of the fungus. After incubating the infected plants for 3 days at 95-100% relative humidity and at 21° C. the fungal infection is evaluated. An important number of the compounds of formula (I), e.g., the compounds nos. 1.9, 1.10, 1.11 and 1.21 completely inhibit the growth of the fungus at a concentration of 0.006% and even below.

EXAMPLE XIII

Activity against *Hemileia vastatrix* on coffee-trees

Residual-protective action:

Coffee-trees, about 15 cm in height, are sprayed with a spray broth (containing 0.06% of active substance) prepared from a wettable powder of the active substance. After 24 hours the treated plants are infected with a suspension of spores of the rust fungus. The infected coffee-plants are stood in a humidity room during 48 hours and then in a glass-house at 22° C. until the appearance of rust-pustules (about 4 weeks). The reduction of the number of rust-pustules is a measure for the activity of the test substances. The compounds of formula (I) display complete protective action at the indicated concentration. The compounds nos. 2.9, 2.10, 2.11, 2.16 and the like display complete protective activity even at a concentration of 0.002%.

EXAMPLE XIV

Residual-protective action against *Venturia inaequalis* on apple seedlings

Apple seedlings, being 10-20 cm in height, are sprayed with a spray broth (containing 0.06% of active substance), prepared from a wettable powder of the active substance. After 24 hours the treated plants are infected with a suspension of conidia of the fungus. The plants are then incubated at 90-100% relative humidity and subsequently during 10 days in a greenhouse at 20°-24° C. The fungal infection is evaluated 15 days after the day of infection. The 1H-1,2,4-triazole derivatives of formula (I) display at the indicated concentration of 0.06% complete protective action. Even at the very low concentration of 0.006%, the compounds nos. 2.9, 2.10, 2.11, 2.16 and similar compounds display complete activity.

EXAMPLE XV

Activity against *Puccinia graminis* on wheat (a) Residual-protective action:

Wheat plants were sprayed 6 days after sowing with a spray broth (0.06% of active substance) prepared from a wettable powder of the active substance. After 24 hours the treated plants were infected with a suspension of Uredospores of the fungus. After an incubation period of 48 hours at 95-100% relative humidity and at about 20° C. the plants were stood in a greenhouse at approx. 22° C. The development of rust-pustules was evaluated 12 days after the infection. The compounds of formula (I) display complete inhibition of the growth of the fungus. Even at a low concentration of 0.006% the compounds nos. 2.10, 2.16, 2.27 and 2.31 display complete inhibition.

(b) Systemic action

5 Days after sowing wheat plants are sprayed with a spray broth (containing 0.006% of active substance; the amount of the spray being proportional with the soil-volume) prepared from a wettable powder of the active substance. After 3 days the treated plants are infected with a suspension of Uredospores of the fungus. After an incubation period of 48 hours at 95-100% relative humidity and at 20° C. the treated plants are stood in a glass-house at about 22° C. The rust-pustules are evaluated 12 days after the day of infection. Certain compounds of formula (I), e.g., the compounds nos. 2.9 and 2.10 completely inhibit the growth of the fungus by systemic action, and, the compound no. 2.11 displays complete activity even at a concentration of 0.002%.

The results of the biological examples IX–XV prove the extraordinary potency and the broad spectrum of activity of the compounds of formula (I), particularly the 1H-1,2,4-triazoleacetals, against biologically different plant pathogenic fungi.

What is claimed is:

1. A chemical compound selected from the group consisting of 1-[2-(2,4-dichlorophenyl)-5,5-diethyl-1,3-dioxan-2-ylmethyl]-1H-1,2,4-triazole and the pharmaceutically acceptable acid addition salts, metal salt complexes and stereochemically isomeric forms thereof.

2. A chemical compound selected from the group consisting of 1-[2-(2,4-dichlorophenyl)-4-methyl-1,3-dioxan-2-ylmethyl]-1H-1,2,4-triazole and the pharmaceutically acceptable acid addition salts, metal salt complexes and stereochemically isomeric forms thereof.

3. A composition for combating fungi comprising an inert carrier material and as an active ingredient an effective antifungal amount of a compound selected from the group consisting of 1-[2-(2,4-dichlorophenyl)-5,5-diethyl-1,3-dioxan-2-ylmethyl]-1H-1,2,4-triazole and the pharmaceutically acceptable acid addition salts, metal salt complexes and stereochemically isomeric forms thereof.

4. A composition for combating fungi comprising an inert carrier material and as an active ingredient an effective antifungal amount of a compound selected from the group consisting of 1-[2-(2,4-dichlorophenyl)-4-methyl-1,3-dioxan-2-ylmethyl]-1H-1,2,4-triazole and the pharmaceutically acceptable acid addition salts, metal salt complexes and stereochemically isomeric forms thereof.

5. A method of combating fungi which comprises contacting said fungi with an effective antifungal amount of a compound selected from the group consisting of 1-[2-(2,4-dichlorophenyl)-5,5-diethyl-1,3-dioxan-2-ylmethyl]-1H-1,2,4-triazole and the pharmaceutically acceptable acid addition salts, metal salt complexes and stereochemically isomeric forms thereof.

6. A method of combating fungi which comprises contacting said fungi with an effective antifungal amount of a compound selected from the group consisting of 1-[2-(2,4-dichlorophenyl)-4-methyl-1,3-dioxan-2-ylmethyl]-1H-1,2,4-triazole and the pharmaceutically acceptable acid addition salts, metal salt complexes and stereochemically isomeric forms thereof.

* * * * *